United States Patent [19]

Pratt, Jr.

[11] Patent Number: 4,848,152

[45] Date of Patent: Jul. 18, 1989

[54] BIOFEEDBACK LIFTING MONITOR

[76] Inventor: G. Andrew Pratt, Jr., 5201 Arbor Glen, The Colony, Tex. 75056

[21] Appl. No.: 45,274

[22] Filed: May 4, 1987

[51] Int. Cl.$^4$ .................... A61B 5/22; A63B 21/24
[52] U.S. Cl. ........................................ 73/379; 272/129
[58] Field of Search .......... 73/379; 272/129, DIG. 4, 272/DIG. 5

[56] References Cited

U.S. PATENT DOCUMENTS

| | | |
|---|---|---|
| 2,290,387 | 7/1942 | Schwartz . |
| 3,020,639 | 2/1962 | Karpovich et al. . |
| 3,424,005 | 1/1969 | Brown . |
| 3,465,592 | 9/1969 | Perrine . |
| 3,572,700 | 3/1971 | Mastropaolo . |
| 3,752,144 | 8/1973 | Weigle, Jr. . |
| 3,869,121 | 3/1975 | Flavell ............................ 272/129 |
| 3,896,672 | 7/1975 | Henson et al. . |
| 3,902,480 | 9/1975 | Wilson . |
| 3,916,876 | 11/1975 | Freeman . |
| 3,929,335 | 12/1975 | Malick . |
| 3,989,240 | 11/1976 | Victor et al. . |
| 4,041,760 | 8/1977 | Henson et al. . |
| 4,050,310 | 9/1977 | Keiser . |
| 4,108,164 | 8/1978 | Hall, Sr. . |
| 4,122,840 | 10/1978 | Tsuchiya et al. . |
| 4,138,106 | 2/1979 | Bradley . |
| 4,184,678 | 1/1980 | Flavell et al. . |
| 4,261,562 | 4/1981 | Flavell . |
| 4,416,293 | 11/1983 | Anderson et al. . |
| 4,436,099 | 3/1984 | Raftopoulos . |
| 4,479,647 | 10/1984 | Smith . |
| 4,492,233 | 1/1985 | Petrofsky et al. . |
| 4,544,154 | 10/1985 | Ariel ................................ 73/379 X |
| 4,549,555 | 10/1985 | Fraser et al. . |
| 4,711,450 | 12/1987 | McArthur .................... 272/DIG. 5 |

Primary Examiner—Charles A. Ruehl
Attorney, Agent, or Firm—Jim Zegeer

[57] ABSTRACT

An apparatus for testing and teaching the lifting capacity and technique of a user includes a brake or clutch for resisting user input force which is controlled by feedback from sensors through a computer. Several operating modes can be chosen, including isometric, isokinetic, isotonic and a special accommodating isotonic which simulates lifting a real object as long as the user exerts enough force, but decreases a resisting force when it is more than the user can handle. A motor is used to substantially eliminate inherent system resistance.

13 Claims, 7 Drawing Sheets

46 FY = FORCE FROM Y-LOAD CELL
47 FZ = FORCE FROM Z-LOAD CELL
48 ANGLE $\theta = \tan^{-1} FZ/FY$
49 USER FORCE $(T) = FZ \sin^{-1}\theta$

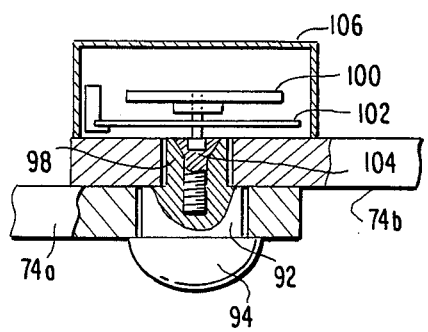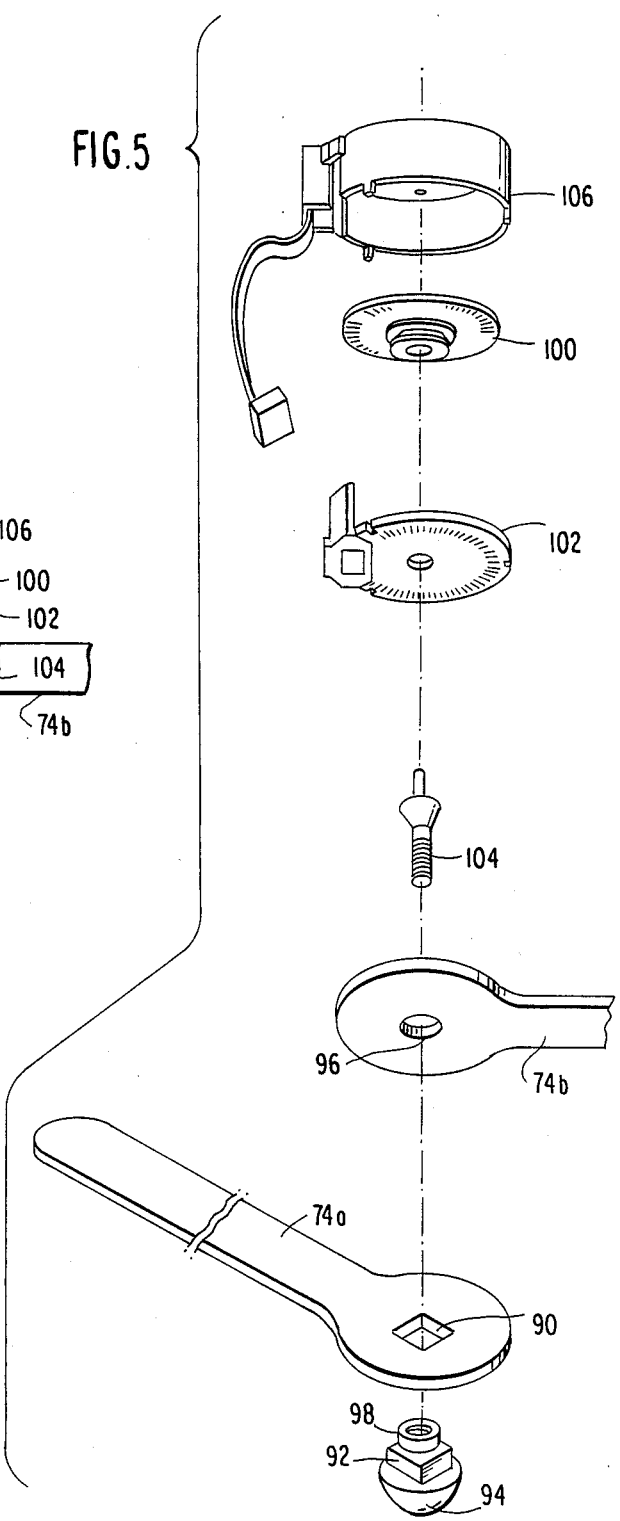

BIOFEEDBACK LIFTING MONITOR

DESCRIPTION

1. Technical Field

The present invention relates generally to an apparatus for measuring a person's lifting capacity, and in particular a clinical apparatus for determining a patient's minimum and maximum lifting capacities. It also relates to apparatus for teaching clinicians and patients proper lifting techniques.

It has been a long-standing problem of clinicians to objectively determine when a patent can return to work following a back injury related to lifting. Clinicians must also determine the potential for re-injuring a patent who has suffered from a back injury related to lifting. The possibility of re-injury has become a growing concern of medical liabiality. A medical clearance with special provisions is frequently required by an employer before an employee can return to work after such a back injury.

It has been a common practice to assign lifting provisions subjectively, such as 20-25 pounds maximum lifting limit. Physical functions assessments are difficult to quantify, and it is likewise difficult to determine if a patient is actually meeting the minimum job requirements. Nonetheless, it is frequently assumed by both the patient and the employer that so long as the patient abides by the lifting provisions, it is safe to return to the work place.

Health related standards have been formulated which require the patient be statistically strength tested in an isometric (no movement) mode. The patient pulls on a strain gauge in a given static posture and the measurement is then compared to a standard. The validity of this approach is repeatedly questioned due to comparing the result of an isometric test in evaluating a dynamic event.

1. Background Art

In recent years, there have been attempts to provide strength testing devices for dynamic testing. Some of these devices would involve developing isokinetic exercise apparatus of which the user moves at a constant velocity regardless of the amount of resistance that is applied. The isokinetic exercise allows the user to move throughout an entire range of motion safely, because the force offered by the apparatus is accommodating to the user force.

Conceptionally, isokinetic exercise is similar to pushing against an air pump piston. If a user could regulate the amount of air exiting the pump, then when the user pushes hard on the air pump, there would be a great amount of back pressure and thus the person would encounter a great amount of resistance. If the user pushes only slightly on the air pump, then the user would encounter only a slight amount of resistance. Whether the user pushes hard or slow against the piston, the piston moves at a substantially constant speed, and thus the accommodating concept of isokinetics. Such devices are shown in U.S. Pat. Nos. 4,041,760 of Henson, et al, 3,896,672 of Henson, et al and 3,465,592 of Perrine.

Another advantage of the isokinetic mode is that it allows a clinician with no prior familarity with the patient's strength capabilities to test the patient by simply placing him or her in an isokinetic mode. The clinician can safely ascertain the patient's strength capabilities. A disadvantage and criticism of the isokinetic mode is, however, that it does not simulate normal movement. A person does not normally move at a constant velocity. In normal lifting, a person accelerates at the beginning of the lifting stroke and decelerates toward the end of the stroke. For this reason, there have been inventions that have addressed the need to operate in an isotonic (constant force) mode. For example, U.S. Pat. No. 3,902,480 of Wilson has provided an electrical-mechanical isotonic or isokinetic exercise system. U.S. Pat. No. 4,184,678 of Flavell et al shows a programmable acceleration excerciser. In this apparatus, Flavell has provided means for the user to choose among a variety of pre-selected acceleration and constant velocity patterns. U.S. Pat. No. 4,138,106 of Bradley shows a weight training apparatus in which the force varies according to the initial acceleration. The user is not, however, able to choose a pre-selected force and accelerate freely in either Flavell or Bradley systems. U.S. Pat. No. 4,544,154 has provided a programmable isokinetic or isotonic system with a feedback loop using hydraulic components. Once the user chooses a pre-selected force at the beginning of the test, the feedback loop maintains that force regardless of the varying velocities.

Although strength measurements are needed in any lifting analysis, the use of a strength testing apparatus alone will not provide the clinician with the information needed in determining a "ready for work" status. The technique of lifting is one of the fundamental determinates to predicting back injury resulting from lifting.

There have been devices which measure joint ranges of motion. U.S. Pat. No. 3,929,335 of Malick was developed for the use of motivating a patient in need of occupational therapy to exercise. It includes his movement and exercise of muscles after a long period of disuse for nerve damage. The exercises are often difficult and the patient must, in many cases, be constantly reminded to continue the exercise.

U.S. Pat. No. 4,108,164 of Hall relates to measuring the range of motion in the back with various activities. It includes a jacket containing clinometers. The sensors are attached to a jacket instead of to the subject. Using this approach, there would be slippage between the jacket and the subject. The degree of slippage depends on how closely the jacket approximates each individual. In addition, in the process of lifting, the concern is not necessarily with the spinal technique but rather in the hip and knee synchronization in general. As an example, during the lifting process, it is important that the knees are flexed substantially enough to allow the user's back to remain near perpendicular to the floor in order to decrease the force on the user's back.

DISCLOSURE OF INVENTION

In accordance with the present invention, an apparatus for testing and teaching the lifting capacity, of the user includes in a preferred form a handle and cable for user input. The user exerts force against the handle which is affixed to the cable. The cable in turn rotates a shaft, but also operates on a force and angle measuring device. The user input force is resisted by some device such as a magnetic particle unit which can be either a brake or clutch. In one form, the testing and teaching apparatus includes a motor operably connected to the shaft for substantially eliminating inherent system resistance to the user input force. Biofeedback is provided to the user by a display device which is positioned for user viewing as the user exerts force against the cable and handle.

In a preferred form, a computer controls the resisting apparatus. The force and angle measuring device as well as the device for measuring the distance over which a user has exerted force are connected in a feedback relationship to the computer. The computer contains four program process steps for operating the computer and program steps for selecting which of the programs operates the computer at a given time. One program for operating the computer produces substantially no movement resulting from input force exerted by a user. A second program produces substantially constant speeds throughout a predetermined portion of movement resulting from input force above a predetermined minimum exerted by user. Yet another program limits the resisting force from the resisting device to a predetermined maximum, and the final program for operating the computer creates a substantially constant resisting force as long as the input force exerted by user is at least a predetermined level and causes the speed of movement resulting from input force exerted by user to be proportional to that force when that force is less than the predetermined level. This particular program or process is referred to for shorthand as an accommodating isotonic feature or mode. It allows a user to choose a pre-selected force and, through a feedback loop in the electronic controller of the apparatus, the force will decrease or increase according to the changes provided by the user. With the accommodating isotonic mode, the user may select a weight to be simulated which acts only while the user is engaging the system. As long as the user is applying a force that is greater than or equal to the pre-selected force, the system will allow the user to freely accelerate or maintain a constant velocity depending upon the force input by the user. If the user begins to decrease the full force, the velocity of the system will decrease until it has reached a full stop. If the user then begins to pull once again, then velocity continues to increase as it would in a naturally occurring event. The system thus combines the safety of the accommodating feature which has been previously available with isokinetics with the isotonic mode of movement.

These and other objects, advantages and features of this invention will be apparent from the following description taken with reference to the accompanying drawing, wherein is shown the preferred embodiments of the invention.

BRIEF DESCRIPTION OF DRAWING

FIG. 5 shows an exploded view of a joint position sensor;

FIG. 6 shows a cross-sectional view of the joint position sensor of Figures;

BEST MODE FOR CARRYING OUT THE INVENTION

Figure 1:
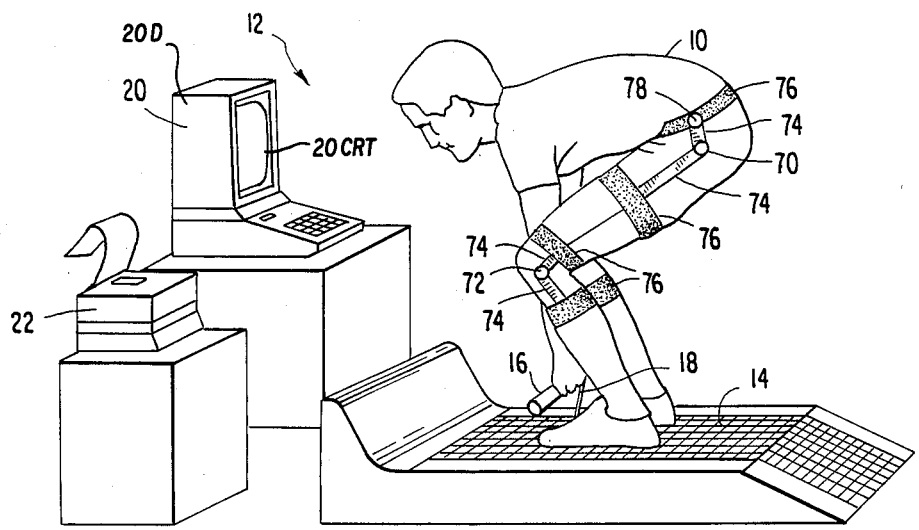
FIG. 1 is a pictorial representation of a user operating the present invention.

Referring now to the drawings and in particular to FIG. 1, a user 10 begins a lift stroke on an apparatus 12 according to the present invention for testing and teaching his lifting capacity and technique. Apparatus 12 includes a platform 14 on which the user stands and some means for accepting user input force including a handle 16 for gripping and cable 18 secured to the handle. User input force can normally be exerted over a predefined distance from the start position until the cable is fully extended, normally with the user in a standing position. A system could also be constructed to allow the user to continue to lift the handle over his head. Means, such as computer 20, is used for controlling and monitoring operation of the apparatus, and a hard copy of the results are provided by printer 22. A visual display 20D has a CRT screen 20CRT positioned for viewing by the user and thereby achieve biofeedback to the user of his lifting technique. This is helpful in teaching clinicians and users proper lifting techniques.

Figure 2:
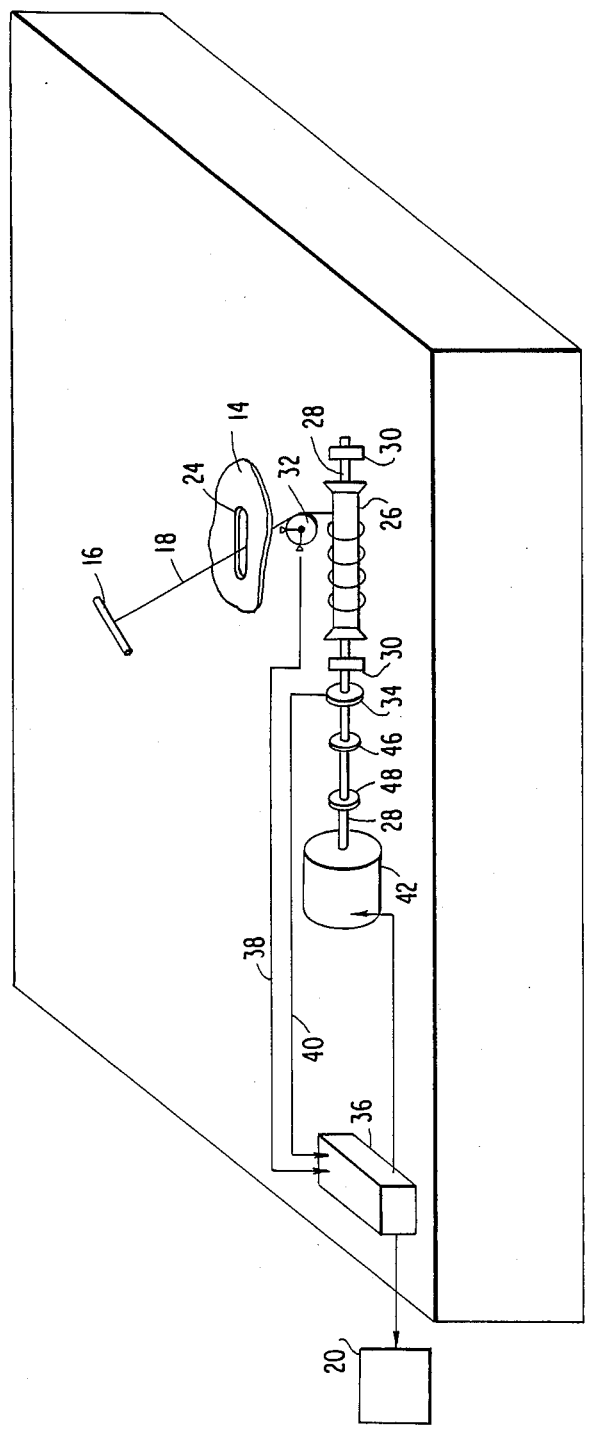
FIG. 2 is a perspective view of a user input means, a resisting clutch or brake, sensors and buffer according to the present invention.

Referring now to FIG. 2, cable 18 extends through a slot 24 of platform 14 and engages a spool 26 which is affixed to a shaft 28 which also forms part of the means for accepting user input force. Cable 18 winds around spool 26, and unwinds as user 10 lifts handle 16, turning shaft 28 as a result. Shaft 28 is rotably held on either side by pillow bearings 30. Cable 18 is also attached to force and angle measuring device 32. Readings from force and angle measuring device 32 as well as a rotation position sensor device 34 are connected in a feedback relationship to computer 20 through buffer 36 by pathways 38 and 40 respectively. Rotation position sensor 34 acts as means for measuring the distance over which a user has exerted force. . Means such as magnetic particle unit brake or clutch 42 is in operably coupled to shaft 28 for resisting user input force. As a user engages the system, shaft 28 rotates so that rotation position sensor which is a shaft optical encoder rotates and movement can be detected. Once the user has reached the top of the lifting stroke, and begins letting handle 16 back down, cable 18 is retracted by rewind coil 46 which operably engages shaft 28. A one-way clutch 48 allows the shaft 28 to rotate in the rewind direction without engaging magnetic particle unit brake or clutch 42.

Figure 3:
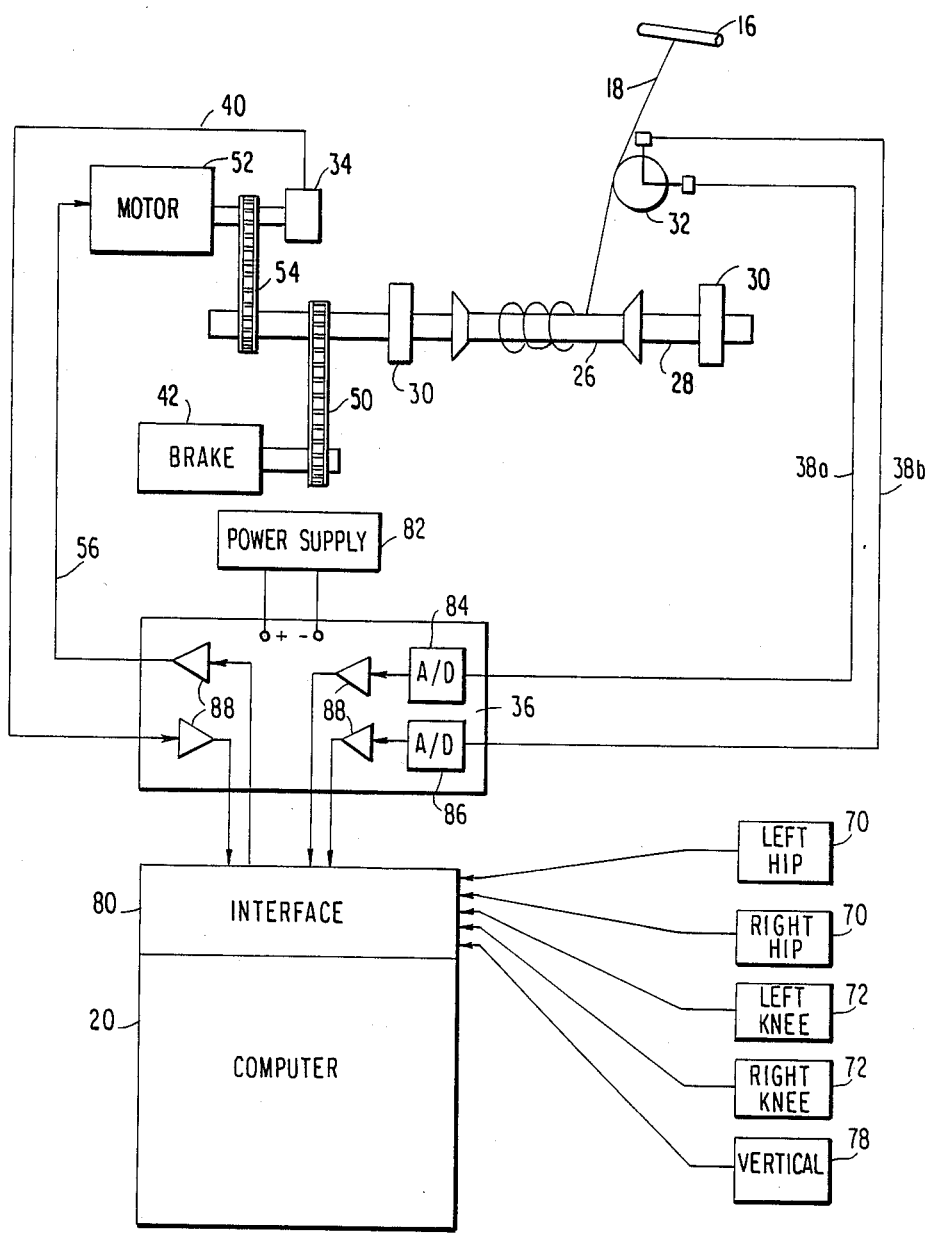
FIG. 3 is a diagrammatic view of the present invention showing means for substantially eliminating inherent system resistance and an alternative method for operably connecting the resistance brake or clutch.

Referring now to FIG. 3, in an alternative arrangement in which like elements are numbered the same as in previous figures, brake or clutch 42 is operably coupled to shaft 28 through a chain and sprocket arrangement 50. Means including motor 52 is operably connected to shaft 28 through chain and sprocket arrangement 54 which also drives rotation position sensor 34. Motor 52 provides a positive rotation to shaft 28 as directed by feedback path 56 in order to substantially eliminate inherent system resistance to user input force. This is distinct from those systems in which a motor provides the resistance in which the rotation force of the motor is negative.

Figure 4:
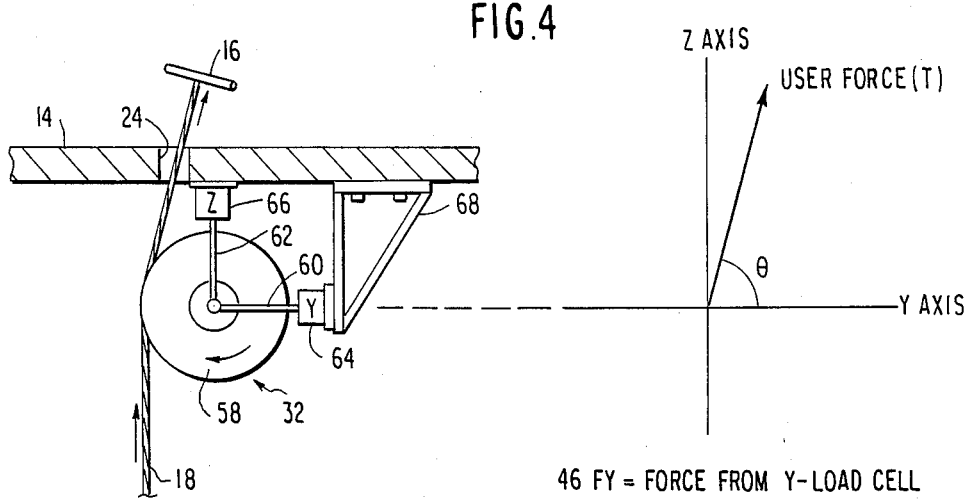
FIG. 4 shows a combination force measuring and angle measuring unit according to the present invention.

Referring also to FIG. 4, force and angle measuring device 32 includes a spool 58 which is driven by cable 18. Spool 58 is rotatably secured by horizontal strut 60 and vertical strut 62 which are affixed to load cells 64 and 66 respectively. Vertical load cell 66 abuts the lower surface of platform 14 and measures the force in the vertical direction. Horizontal load cell 64 abuts a bracket 68 which is firmly affixed to the bottom surface of platform 14, for measuring load in the horizontal direction.

Referring now to both FIG. 1 and FIG. 3, hip positions sensors 70 and knee positions sensors 72 are attached to the body of user 10 by means of lever arms 74 and cuff straps 76. Vertical sensor 78 is attached to the waist of cuff strap. Inputs from all of these sensors are then fed to computer interface card 80, although buffering may be necessary. The computer interface card 80 also receives inputs from rotation position sensor 34 as well as horizontal and vertical load cells 64 and 66 which have been processed through buffer 36. Buffer 36 receives electrical power from power supply 82 both to provide power to handle all traditional converters 84 and 86 for converting the analog signal of the load cells to digital signals to be accepted by interface 80 and also for buffer amplifiers 88.

Referring also to FIG. 5 and FIG. 6, lower lever arm 74a forms a square opening 90 for receiving square head 92 of nut 94. Upper lever arm 74b forms a circular opening 96 for receiving circular head 98. It can thus be seen movement of lower lever arm 74a will in turn rotate code wheel assembly 100 of an optical motion encoder. Emitter assembly 102 of the optical motion encoder is affixed to upper level arm 74b so that when lever arm 74a rotates with respect to lever arm 74b code wheel assembly 100 rotates with respect to emitter assembly 102. Bolt 104 rotatably connects the two lever arms. Encoder body 106 of the optical motion encoder houses the rest of the encoder and contains the phase place lens and detectors. The entire optical motion and coder is the type that is commercially available and is also of a type similar to what is suitable for rotation position sensor 34 (FIG. 3).

Figure 7:
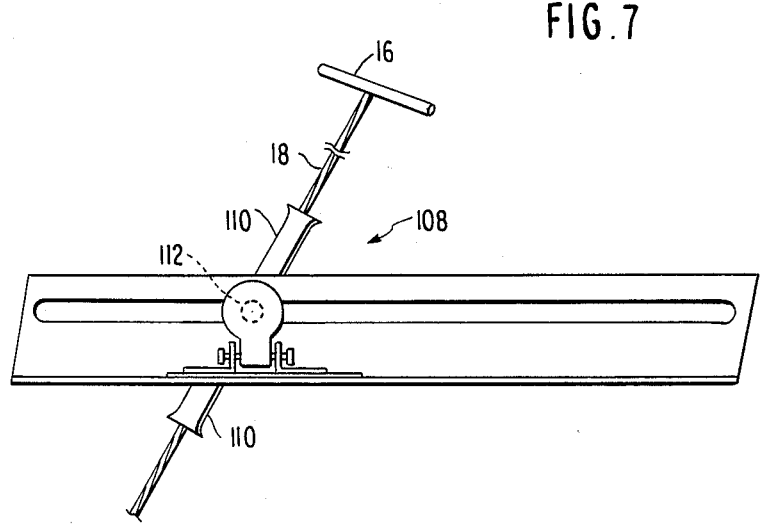
FIG. 7 is a right side elevational view of an alternative embodiment of an angle measuring device according to the present invention.
Figure 8:
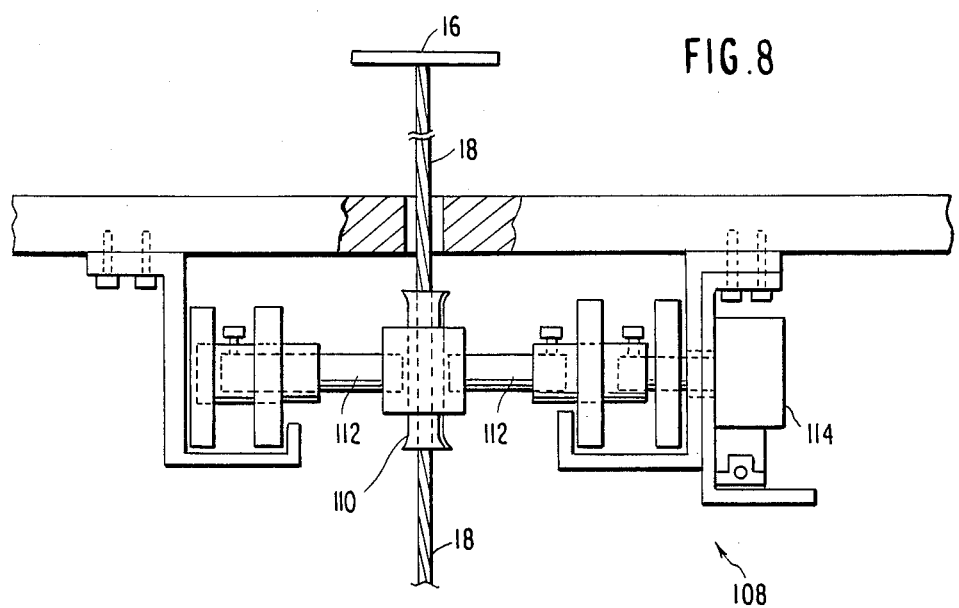
FIG. 8 is a front elevational cross-sectional view of the cable direction sensor of FIG. 7.

Referring now to FIG. 7 and FIG. 8, an alternative embodiment of angle measuring device according to the present invention is referred to generally by reference numeral 108. Angle measuring device includes a tube 110 through which cable 18 is pulled. Tube 110 is secured to shaft 112 which is rotatably mounted along an axis perpendicular to the tube. Rotation of shaft 112, in turn, rotates the code wheel assembly within an optical encoder 114. Movement of the angle pull of cable 18 thus rotates tube 110 about the axis of shaft 112 which in turn registers on optical encoder 114.

Figure 9:
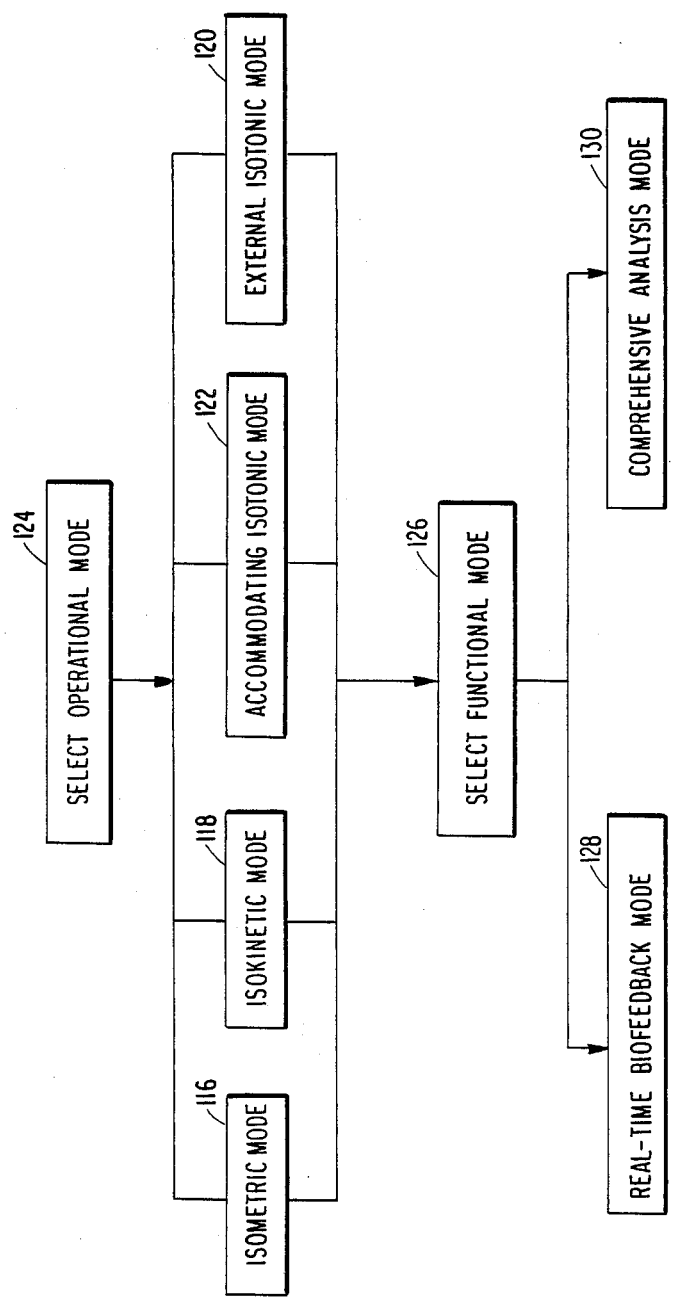
FIG. 9 is a diagrammatic view of a lifting apparatus selection and operational modes according to the present invention.

Referring now to FIG. 9, an apparatus according to the present invention for testing and teaching the lifting capacity and technique of a user includes means such as programmable isometric mode means 116 for operating computer 20 to produce substantially no movement of cable 18 resulting from input force exerted by user on handle 16. Means such as program isokinetic mode means 118 operates computer 20 to produce substantially constant speed of motion of cable 18 throughout a predetermined portion of movement resulting from input force exerted on handle 16 being above a predetermined minimum. Means such as program external isotonic mode means 120 operates on computer 20 to limit the resisting force of brake or clutch 42 to a predetermined maximum. Finally, means such as program accommodating isotonic mode means 122 operates computer 20 wherein the resisting force of brake or clutch 42 is substantially constant as long as the input force exerted by user is at least a predetermined level and wherein the resisting force varies as a function of the force, such as directly proportional to the force or a power of the force exerted, by user when the user force is less than the predetermined level. Means such as program select operational mode means selects which of the operating mode means 116, 118, 120 or 122 operates the computer.

A select functional mode 126 selects between real-time biofeedback mode 128 and a comprehensive analysis mode 130.

Figure 10:
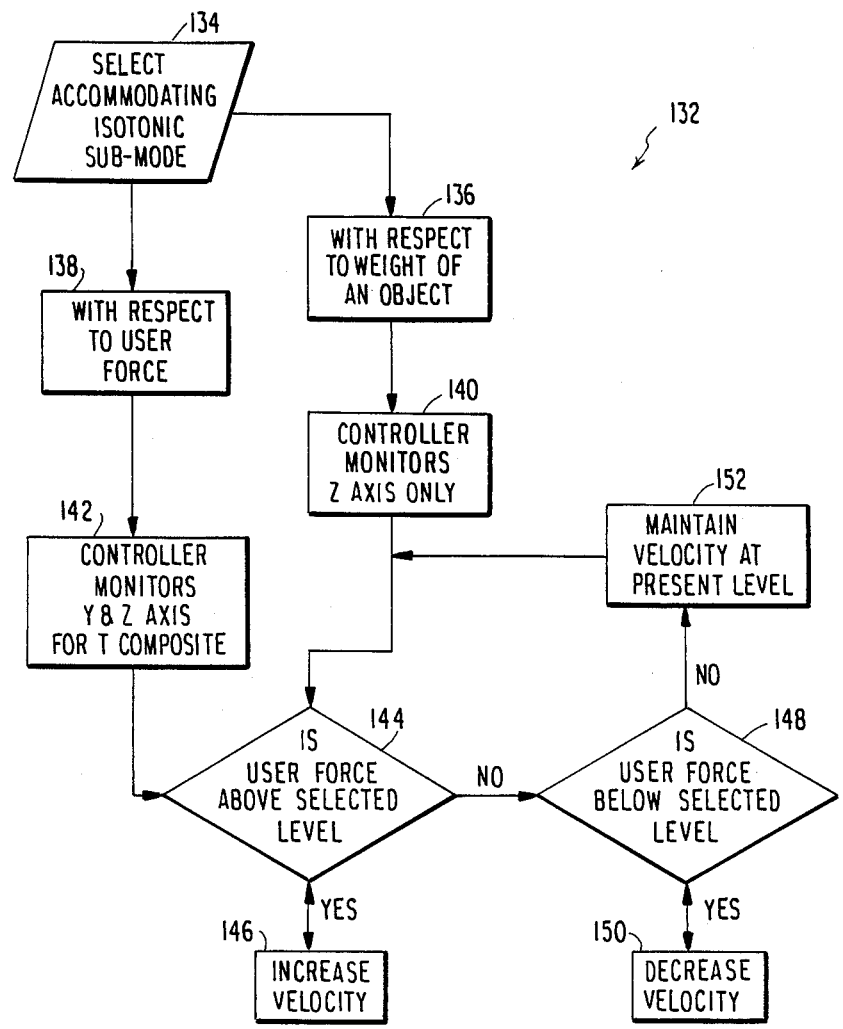
FIG. 10 is a flow chart of a method for testing and teaching lifting capacity and technique according to the present invention.

Referring now to FIG. 10, a method according to the present invention for testing and teaching the lifting capacity and technique of a user is referred to generally by reference numeral 132. When an accommodating isotonic mode is selected 122, the weight of an object is determined 136 provided the force exerted by user is above a predetermined level. If the user force is below that predetermined level, then the force is with respect to the user force 138. If the weight of the object is selected by virtue of the user force being above the predetermined minimum level, then the controller monitors only force in the vertical direction 140. If, on the other hand, the user cannot exert the minimum force, then the controller monitors both the vertical and horizontal components of force 142 in order to determine both the efficiency of user technique and to prevent possible injury to the user. At that point, the process is continuously monitored to see if the user force is above the selected minimum level 144. If it is, then the velocity is allowed to increase 146 just as it would if the user were lifting a real object. If the user force is not above the selected level, then it is checked to see if it is below the selected level 148. If it is below the selected level, then the velocity is decreased 150. If, on the other hand, the user force is not below the selected level, then at this point it is exactly at the selected level and the velocity is maintained constant 152.

From the foregoing it will be seen that this invention is one well adapted to the attain all the ends and objects hereabove set forth, together with other advantage which are obvious and which are inherent to the apparatus. It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the figures of the accompanying drawing is to be interpreted as illustrative and not in a limiting sense.

I claim:

1. An apparatus for testing and teaching the lifting capacity and technique of a user, comprising in combination:
    means for accepting user input force exerted over a predetermined distance,
    means for resisting user input force,
    means for controlling the resisting means, means for operating the controlling means to produce substantially no movement resulting from input force exerted by a user, means for operating the controlling means to produce substantially constant speed throughout a predetermined portion of movement resulting from input force above a predetermined minimum exerted by a user, means for operating the controlling means to limit the resisting force of the resisting means to a predetermined maximum, means for selecting which of the means for operating operates the controlling means, and, means for operating the controlling means wherein the resisting force is substantially constant as long as the input force exerted by a user is at least a predetermined level and wherein the resisting force varies as a function of the force exerted by a user when the user force is less than the predetermined level.

2. An apparatus according to claim 1 further comprising means for substantially eliminating inherent system resistance to user input force, operably connected to the means for accepting user input force whereby the force exerted by the resisting means substantially equals the force exerted by a user.

3. An apparatus according to claim 2 further comprising means for measuring the distance over which a user has exerted force, connected in a feedback relationship to the controlling means.

4. An apparatus according to claim 1 wherein the force accepting means comprises a shaft which rotates in response to the exertion of user input force over a distance and wherein the resisting means comprises a magnetic particle unit operably coupled to the shaft.

5. An apparatus according to claim 1 further comprising means for substantially eliminating inherent system resistance to user input force, operably connected to the means for accepting user input force whereby the force exerted by the resisting means substantially equals the force exerted by a user.

6. An apparatus according to claim 5 wherein the force accepting means comprises a shaft which rotates in response to the exertion of user input force over a distance and wherein the resisting means comprises a magnetic particle unit operably coupled to the shaft, and wherein the resistance eliminating means comprises a motor operably coupled to the shaft.

7. An apparatus for testing and teaching the lifting capacity and technique of a user, comprising in combination:

means for accepting user input force exerted over a pre-defined distance,
means for resisting user input force,
controlling means for controlling the resisting means,
program means for operating the controlling means to produce substantially no movement resulting form input force exerted by a user,
program means for operating the controlling means to produce substantially constant speed throughout a predetermined portion of movement resulting from input force above a predetermined minimum exerted by a user,
program means for operating the controlling means to limit the resisting force from the resisting means to a predetermined maximum,
means for selecting which of the program means operates the controlling means, and
a further program means for operating the controlling means wherein the resisting force is substantially constant as long as the input force exerted by a user is at least a predetermined level and wherein the resisting force varies as a function of the input force exerted by a user when the user force is less than the predetermined minimum.

8. An apparatus according to claim 7 further comprising means for substantially eliminating inherent system resistance to user input force, operably connected to the means for accepting user input force whereby the force exerted by the resisting means substantially equals the force exerted by a user.

9. An apparatus according to claim 8 further comprising means for measuring the distance over which a user has exerted force, connected in a feedback relationship to the controlling means.

10. An apparatus according to claim 7 wherein the force accepting means comprises a shaft which rotates in response to the exertion of user input force over a distance and wherein the resisting means comprises a magnetic particle unit operably coupled to the shaft.

11. An apparatus according to claim 7 further comprising means for substantially eliminating inherent system resistance to user input force, operably connected to the means for accepting user input force whereby the force exerted by the resisting means substantially equals the force exerted by a user.

12. An apparatus according to claim 11 wherein the force accepting means comprises a shaft which rotates in response to the exertion of user input force over a distance and wherein the resisting means comprises a magnetic particle unit operably coupled to the shaft, and wherein the resistance eliminating means comprises a motor operably coupled to the shaft.

13. A method for testing and teaching the lifting capacity of a person, comprising in combination the steps of:

accepting user input force over a predefined distance;
resisting the user input force;
controlling the amount of resisting force wherein the resisting force is substantially constant as long as the input force exerted by the person is at least a predetermined level; and
controlling the amount of resisting force wherein the speed of movement resulting from the input force exerted by the person is proportional to that force when that force is less than the predetermined level.

* * * * *